United States Patent
Ishizuka et al.

(10) Patent No.: US 9,517,267 B2
(45) Date of Patent: Dec. 13, 2016

(54) PHOTODYNAMIC DIAGNOSTIC AGENT AND PHOTOBLEACHING INHIBITOR

(71) Applicants: SBI Pharmaceuticals Co., Ltd., Tokyo (JP); Tokyo Institute of Technology, Tokyo (JP)

(72) Inventors: Masahiro Ishizuka, Tokyo (JP); Tohru Tanaka, Tokyo (JP); Shun-ichiro Ogura, Tokyo (JP); Takuya Ishii, Tokyo (JP)

(73) Assignees: SBI Pharmaceuticals Co., Ltd., Tokyo (JP); Tokyo Institute of Technology, Tokyo (JP)

( * ) Notice: Subject to any disclaimer, the term of this patent is extended or adjusted under 35 U.S.C. 154(b) by 64 days.

(21) Appl. No.: 14/373,341

(22) PCT Filed: Jan. 22, 2013

(86) PCT No.: PCT/JP2013/051131
§ 371 (c)(1),
(2) Date: Jul. 18, 2014

(87) PCT Pub. No.: WO2013/111719
PCT Pub. Date: Aug. 1, 2013

(65) Prior Publication Data
US 2015/0297720 A1    Oct. 22, 2015

(30) Foreign Application Priority Data
Jan. 26, 2012 (JP) ................................. 2012-014135

(51) Int. Cl.
| | | |
|---|---|---|
| *A61K 41/00* | (2006.01) | |
| *C07C 69/84* | (2006.01) | |
| *A61K 45/06* | (2006.01) | |
| *A61K 49/00* | (2006.01) | |
| *A61K 31/192* | (2006.01) | |
| *A61K 31/216* | (2006.01) | |

(52) U.S. Cl.
CPC ......... *A61K 41/0061* (2013.01); *A61K 31/192* (2013.01); *A61K 31/216* (2013.01); *A61K 41/0057* (2013.01); *A61K 45/06* (2013.01); *A61K 49/0036* (2013.01); *C07C 69/84* (2013.01)

(58) Field of Classification Search
CPC .... A61K 47/4806; A61K 49/00; A61K 41/00; A61K 31/221; A61K 31/235
See application file for complete search history.

(56) References Cited

U.S. PATENT DOCUMENTS

| | | | | |
|---|---|---|---|---|
| 5,520,905 A | * | 5/1996 | Uhlmann ................. | A61K 8/44 424/59 |
| 6,180,666 B1 | * | 1/2001 | Wacher ................ | A61K 31/235 514/456 |
| 6,750,212 B2 | * | 6/2004 | Peng .................. | A61K 41/0071 514/185 |
| 2010/0137439 A1 | * | 6/2010 | Wulf ..................... | A61K 31/221 514/561 |

OTHER PUBLICATIONS

Judit Jakus et al., Photosensitizers and antioxidants: a way to new drugs, Photochem. Photobiol. Sci., 2005, 4, 694-698.*
Haim Giloh et al., Fluorescence Microscopy: Related Photobleaching of Rhodamine and Fluorescein Protein conjugates by n-propyl gallate, Science, 1982, 217(24, 1252-1255.*
P. Bryon et al., "Comparison of Anti-fading Agents Used in Fluorescence Microscopy: Image Analysis and Laser Confocal Microscopy Study", The Journal of Histochemistry and Cytochemistry, 1993, vol. 41, No. 12, pp. 1833-1840.
Stummer W. et al., "Intraoperative detection of amlignant gliomas by 5-aminolevulinic acid-induced porphyrin fluorescence", Neurosurgery, 1998, vol. 42, No. 3, pp. 518 to 526, ISSN: 0148-396X.
Gaigalas A.K. et al., Photodegradation of Fluorescein in Solutions Containing n-Propyl Gallate., Journal of Physical Chemistry. A, 2004, vol. 108, No. 20, pp. 4378 to 4384, ISSN: 1089-5639.
Giloh H. et al., Fluorescence microscopy: reduced photobleaching of rhodamine and fluorescein protein conjugates by n-propyl gallate., Science, 1982, vol. 217, No. 4566, pp. 1252 to 1255, ISSN: 0036-8075.
International Search Report Corresponding to International Application No. PCT/JP2013/051131; Date of Mailing: Mar. 5, 2013; 2 Pages.
Krenik K.D. et al., Comparison of antifading agents used in immunofluorescence., Journal of Immunological Methods, 1989, vol. 117, No. 1, pp. 91 to 97, ISSN: 0022-1759.
Tonn J.C. et al., Fluorescence-guided resection of malignant gliomas using 5-aminolevulinic acid: practical use, risks, and pitfalls., Clinical Neurosurgery, 2008, vol. 55, pp. 20 to 26, ISSN: 0069-4827.
White J.C. et al., Photostability studies of phycobiliprotein fluorescent labels., Analytical Biochemistry, 1987, vol. 161, No. 2, pp. 442 to 452, ISSN: 0003-2697.
Widengren J. et al., Strategies to improve photostabilities in ultrasensitive fluorescence spectroscopy., Journal of Physical Chemistry. A, 2007, vol. 111, No. 3, pp. 429 to 440, ISSN: 1089-5639.
Yoshinaga Kajimoto et al., "Unsolved Problems in 5-aminolevulinic Acid Based Photodynamic Diagnosis: Quantification of Fluorescence and Molecular Mechanism of Porphyrin Accumulation", The Journal of Japan Society for Laser Surgery and Medicine, 2011, vol. 32, No. 2, pp. 143 to 148, ISSN: 0288-6200.
McGraw-Hill Dictionary of Scientific and Technical Terms, $5^{th}$ Edition, 1994, Sybil Parker, p. 1197.
Wikipedia, online encyclopedia, "Protoporphyrin IX", Definition from Wikipedia.org. Retrieved Jul. 18, 2016, 3 pages.

* cited by examiner

Primary Examiner — Michael G Hartley
Assistant Examiner — Jagadishwar Samala
(74) Attorney, Agent, or Firm — Myers Bigel, P.A.

(57) ABSTRACT

The objects of the present invention are to inhibit photobleaching of porphyrins as well as to provide a superior photodynamic diagnostic agent and a photodynamic diagnostic method employing the photobleaching inhibitor for porphyrins. The present invention provides a photodynamic diagnostic agent containing a precursor of porphyrins and a gallic acid. The present invention also provides a photobleaching inhibitor for porphyrins containing a gallic acid.

12 Claims, 12 Drawing Sheets

PHOTODYNAMIC DIAGNOSTIC AGENT AND PHOTOBLEACHING INHIBITOR

STATEMENT OF PRIORITY

This application is a 35 U.S.C. §371 national phase application of International Application Serial No. PCT/JP2013/051131, filed Jan. 22, 2013, which claims the benefit, under 35 U.S.C. §119 (a) of Japanese Patent Application No. 2012-014135, filed Jan. 26, 2012, the entire contents of each of which are incorporated by reference herein.

TECHNICAL FIELD

The present invention relates to a photodynamic diagnostic agent and a photobleaching inhibitor, more particularly to a photodynamic diagnostic agent containing a precursor of porphyrins and a gallic acid. The present invention also relates to a detection method employed for photodynamic diagnosis and a photodynamic diagnostic method.

BACKGROUND ART

Various measurements employing fluorescent substances are performed in the field of chemistry. Moreover, in fields such as biotechnology, medicine, and medical care, cells etc. are stained by a fluorescent substance and observed under a fluorescence microscope. Fluorescence assays play an important role in these researches.

Further, in the field of medical care, photodynamic diagnosis (hereinafter abbreviated as PDD) in which a compound that reacts to light (a photosensitizer) is administered and light is irradiated in order to specify the target site is recently gaining attention as a diagnostic method for diseased tissues such as cancer, warts, and acnes. Photodynamic diagnosis (PDD) is, for example, a diagnostic method that specifies the presence or absence of illnesses and affected sites by administering a porphyrin- or a chlorin-based photosensitizer to a patient, allowing this to be accumulated at the diseased tissue, irradiating light at a wavelength of around 400 nm to allow emission of fluorescence, and observing this. Photodynamic diagnosis (PDD) has the advantage of placing less burden on patients by virtue of low invasion and less side effects compared to prior diagnostic methods.

In addition, a method is also being developed in which 5-aminolevulinic acids (ALAs) are administered as the photosensitizer employed in this photodynamic diagnosis (PDD) instead of administering a porphyrin-based photosensitizer. 5-aminolevulinic acid (ALA) is a type of amino acid, and is a substance that is the sole source material of porphyrins essential for plant chlorophyll, heme in animal blood, or the like. It is known that in animals, 5-aminolevulinic acid is metabolized to porphobilinogen, hydroxymethylbilane, uroporphyrinogen coproporphyrinogen III, protoporphyrinogen IX, and protoporphyrin IX in that order, protoporphyrin coordinates with an iron ion to become a heme, and heme binds with a globin to become a hemoglobin.

Porphyrins are known to be incorporated by tumor cells and accumulated. On the other hand, ALAs are known to be incorporated by tumor cells and accumulated in protoporphyrin IX state via said metabolic pathway. Regardless of which administration is taken, the fluorescence of porphyrin is measured to specify the tumor site for diagnosis.

However, porphyrins employed as a photosensitizer develop photobleaching (also referred to as fluorescence discoloration, fluorescence fading) upon fluorescence measurement, and a decrease in fluorescence intensity is observed over time. Photobleaching is a chemical reaction seen on rare occasions with excited fluorescent dye molecules. This reaction occurs because the fluorescent substance in an excited state becomes chemically activated and unstable compared to the ground state. As a result of this reaction, the fluorescent molecule ultimately becomes a low fluorescent structure. For example, in the case of protoporphyrin IX (hereinafter abbreviated as PpIX), there was a problem that the time frame for diagnosis by fluorescence will be short since fluorescence decreases very rapidly, e.g. fluorescence intensity is reduced to one tenth or less in 60 seconds. Accordingly, a method for inhibiting this photobleaching has been desired. However, a method for inhibiting photobleaching of porphyrins has not been known well.

In the meantime, FITC is listed as a fluorescent substance well-employed in fields such as chemistry and biotechnology. In regards to decrease in FITC fluorescence, there is an example of investigating the effect of inhibiting fluorescence decrease with three types of compounds, p-paraphenylenediamine (referred to as PPD), n-propylgallate (referred to as NPG), or 1,4-diazabicyclo[2.2.2]octane (referred to as DABCO) (see Non-Patent Literature 1). However, it was unknown whether or not these compounds exert a similar effect on porphyrins, which are different fluorescent substances having totally differing structure.

CITATION LIST

[Non-Patent Literature 1] P. Bryon et al., "Comparison of Anti-fading Agents Used in Fluorescence Microscopy: Image Analysis and Laser Confocal Microscopy Study," The Journal of Histochemistry and Cytochemistry, 1993, Vol. 41, No. 12, p. 1833-1840

SUMMARY OF THE INVENTION

Problems to be Solved by the Invention

The objects of the present invention are to inhibit photobleaching of porphyrins as well as to provide a superior photodynamic diagnostic agent and a photodynamic diagnostic method employing the photobleaching inhibitor for porphyrins.

Means for Solving the Problems

The present inventors focused on the fact regarding porphyrins that when light is irradiated on porphyrins, it is autoxidated and degraded by the reactive oxygen species produced, and hypothesized that the use of a reductant could block the degradation of porphyrins and inhibit photobleaching. The present inventors surprisingly found that gallic acids have a superior effect of inhibiting photobleaching of PpIX. On the other hand, reductants such as PPD, DABCO, ascorbic acid, or tocopherol had no or almost no effect. The present inventors further found that when ALAs were employed as the precursor of porphyrins, a photobleaching inhibitory effect for PpIX is also obtained by employing a gallic acid.

In other words, the present invention relates to a photodynamic diagnostic agent containing a precursor of porphyrins and a gallic acid for administration at simultaneous or different times.

The photodynamic diagnostic agent of the present invention may be those wherein said gallic acid is an alkyl gallate ester or a salt thereof.

The photodynamic diagnostic agent of the present invention may be those wherein said gallic acid is a compound shown by the following formula (I):

[Chemical Formula 1]

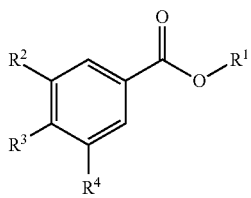

(I)

(wherein $R^1$ is selected from the group consisting of an alkyl group having 1-10 carbons, a cycloalkyl group having 3-8 carbons, an aryl group having 6-14 carbons, and an aralkyl group having 7-15 carbons, and $R^2$, $R^3$, and $R^4$ each represent a hydroxyl group)
or a salt thereof.

The photodynamic diagnostic agent of the present invention may be those wherein in said formula (I), $R^1$ is selected from the group consisting of a methyl group, a propyl group, a butyl group, and an octyl group.

The photodynamic diagnostic agent of the present invention may be those wherein said precursor of porphyrins is ALAs.

The photodynamic diagnostic agent of the present invention may be those wherein said ALAS is a compound shown by the following formula (II):

[Chemical Formula 2]

$$R^1-NHCH_2COCH_2CH_2COOR^2 \quad (II)$$

(wherein $R^1$ represents a hydrogen atom or an acyl group, and $R^2$ represents a hydrogen atom, a linear or branched alkyl group, a cycloalkyl group, an aryl group, or an aralkyl group)
or a salt thereof.

The photodynamic diagnostic agent of the present invention may be those wherein in said formula (II),
$R^1$ is selected from the group consisting of a hydrogen atom, an alkanoyl group having 1-8 carbons, and an aroyl group having 7-14 carbons, and
$R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

The photodynamic diagnostic agent of the present invention may be those wherein in said formula (II),
$R^1$ is selected from the group consisting of a hydrogen atom, a formyl group, an acetyl group, a propionyl group, and a butyryl group, and
$R^2$ is selected from the group consisting of a hydrogen atom, a methyl, an ethyl, a propyl, a butyl, and a pentyl group.

The photodynamic diagnostic agent of the present invention may be those wherein in said formula (II),
$R^1$ is a hydrogen atom, and
$R^2$ is selected from the group consisting of a hydrogen atom, a methyl, an ethyl, a propyl, a butyl, and a pentyl group.

The photodynamic diagnostic agent of the present invention may be those wherein in said formula (II),
$R^1$ is a hydrogen atom, and
$R^2$ is a hydrogen atom.

In another aspect of the present invention, the present invention relates to a photobleaching inhibitor for porphyrins having as the active ingredient a compound shown by the following formula (I):

[Chemical Formula 3]

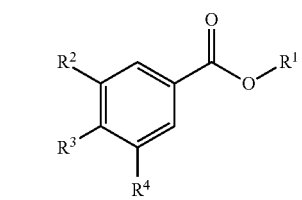

(I)

(wherein $R^1$ is selected from the group consisting of an alkyl group having 1-10 carbons, a cycloalkyl group having 3-8 carbons, an aryl group having 6-14 carbons, and an aralkyl group having 7-15 carbons, and $R^2$, $R^3$, and $R^4$ each represent a hydroxyl group)
or a salt thereof.

The photobleaching inhibitor of the present invention may be those wherein said porphyrins is selected from the group consisting of protoporphyrin IX, uroporphyrin I, uroporphyrin III, coproporphyrin I, coproporphyrin III, heptacarboxylporphyrin I, heptacarboxylporphyrin III, hexacarboxylporphyrin hexacarboxylporphyrin III, pentacarboxylporphyrin pentacarboxylporphyrin III, isocoproporphyrin, harderoporphyrin, isoharderoporphyrin, mesoporphyrin IX, deuteroporphyrin IX, and pemptoporphyrin.

The photobleaching inhibitor of the present invention may be those wherein said porphyrins is protoporphyrin IX (PpIX).

In another aspect of the present invention, the present invention relates to a method for detecting the porphyrins accumulation site comprising the following steps:
a step of irradiating the excitation light for porphyrins to a subject who has been administered in advance a precursor of porphyrins and a gallic acid at simultaneous or different times, and
a step of detecting the fluorescence of porphyrins.

In another aspect of the present invention, the present invention relates to a photodynamic diagnostic method comprising the following steps:
a step of administering a precursor of porphyrins and a gallic acid to a subject at simultaneous or different times,
a step of irradiating the excitation light for porphyrins to the subject,
a step of detecting the fluorescence of porphyrins, and
a step of deciding the porphyrins accumulation site based on the detected fluorescence of porphyrins and determining the range of lesion site.

The photodynamic diagnostic method of the present invention may be those wherein said lesion site is a tumor.

The photodynamic diagnostic method of the present invention may be those wherein said subject is a non-human animal.

The photodynamic diagnostic method of the present invention may be those wherein said precursor of porphyrins is ALAs.

Effects of the Invention

The present invention provides a photobleaching inhibitor for porphyrins. By using the photobleaching inhibitor of the present invention, photobleaching upon administration of porphyrins or their source material ALAs is inhibited, and fluorescence intensity for detection in a photodynamic diagnosis can be maintained for a longer duration and at a greater intensity.

Moreover, ALA is a compound that is present in animal and plant cells, does not possess photosensitization action per se, is selectively incorporated into the lesion site when excessively administered into cells, produces a porphyrin-based compound having photosensitization action, in particular protoporphyrin IX in the heme biosynthetic pathway in cells, and has a nature of being accumulated in cells.

In the present invention, by employing ALAs and a photobleaching inhibitor in combination, side effects can be reduced compared to when porphyrins are used as the photosensitizer, and fluorescence intensity in photodynamic diagnosis can be maintained for a longer duration and at a greater intensity than conventional.

BRIEF DESCRIPTION OF THE DRAWINGS

In FIG. 3, the intensity of the excitation light was 0.1 mA, 0.2 mA, 0.3 mA, and 0.4 mA, respectively.

DESCRIPTION OF EMBODIMENTS

Figure 1:
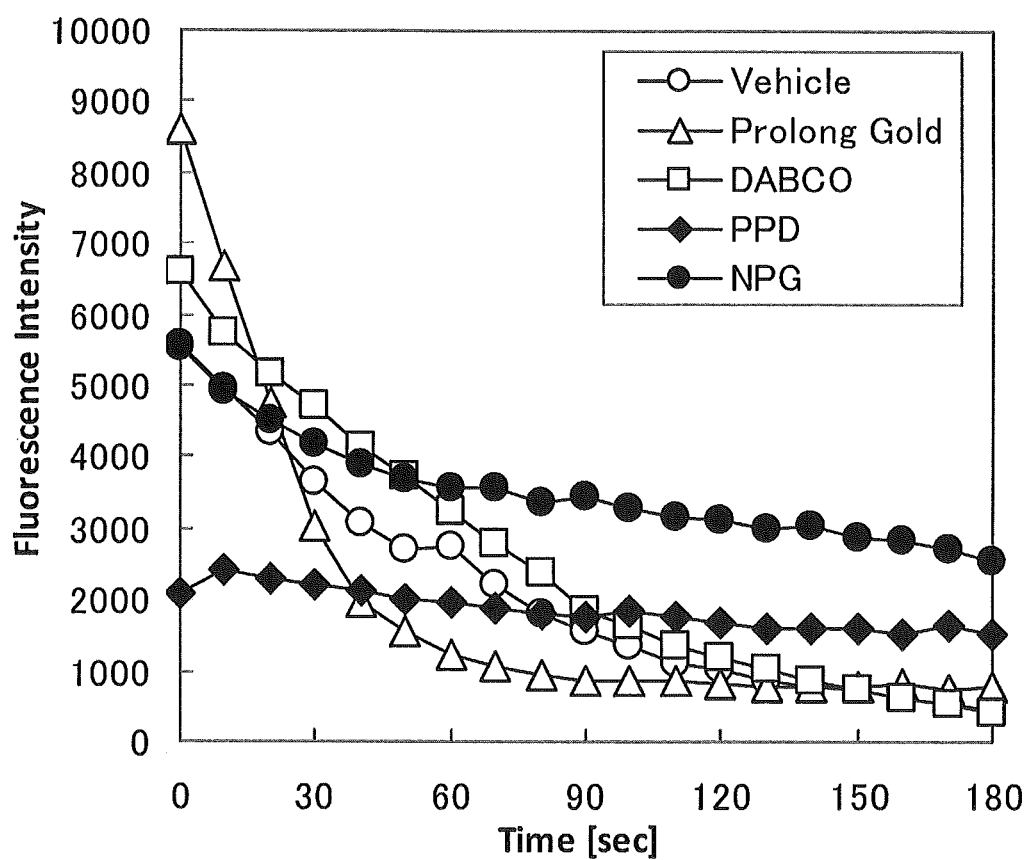
FIG. 1 shows the plot of the fluorescence intensity for every 10 seconds from 0 to 180 seconds post irradiation of excitation light in regards to the transition of fluorescence intensity of PpIX in the presence of each reductant when ALAs and gallic acids or other reductants were incorporated in to cells.

The photobleaching inhibitor for porphyrins of the present invention is not particularly limited, as long as it contains a gallic acid and has a photobleaching inhibitory effect for porphyrins. In the photodynamic diagnostic agent of the present invention, the gallic acid can be administered after, simultaneously, or before administering the precursor of porphyrins.

Gallic acids herein refer to a gallic acid or a derivative thereof or a salt thereof. Gallic acid is also referred to as 3,4,5-trihydroxybenzoic acid, and is contained in many plants such as nutgall, gallnut, hamamelis, tea leaves, and oak bark. Examples of gallic acid derivatives include compounds having the carboxyl group esterified. The gallic acid ester may be an alkyl ester as well as a cycloalkyl ester, an aryl ester, an aralkyl ester, and the like.

In one aspect of the present invention, gallic acids include an alkyl gallate ester.

In the present invention, the gallic acid derivative may be a compound represented by the following formula (I):

[Chemical Formula 4]

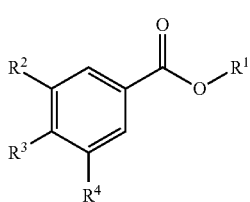

(I)

(wherein $R^1$ represents a group selected from the group consisting of an alkyl group having 1-10 carbons, a cycloalkyl group having 3-8 carbons, an aryl group having 6-14 carbons, and an aralkyl group having 7-15 carbons, and $R^2$, $R^3$, and $R^4$ each represent a hydroxyl group.)

The alkyl group of $R^1$ in said formula (I) can include a linear or branched alkyl group having 1-10 carbons such as a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group, an octyl group, a nonyl group, and a decyl group.

The cycloalkyl group of $R^1$ in said formula (I) can include a cycloalkyl group having 3-8 carbons which may be saturated or have partially unsaturated bonds present, such as a cyclopropyl, a cyclobutyl, a cyclopentyl, a cyclohexyl, a cycloheptyl, a cyclooctyl, a cyclododecyl, and a 1-cyclohexenyl group.

The aryl group of $R^1$ in said formula (I) can include an aryl group having 6-14 carbons such as a phenyl, a naphthyl, an anthryl, and a phenanthryl group.

The aralkyl group of $R^1$ in said formula (I) can be exemplified with the same aryl groups as above as the aryl moiety and the same alkyl groups as above as the alkyl moiety, and can specifically include an aralkyl group having 7-15 carbons such as a benzyl, a phenethyl, a phenylpropyl, a phenylbutyl, a benzhydryl, a trityl, a naphthylmethyl, and a naphthylethyl group.

In one aspect of the present invention, a compound wherein in said formula (I):
$R^1$ is an alkyl group having 1-10 carbons, and
$R^2$, $R^3$, and $R^4$ are a hydroxyl group
is preferred as the gallic acid derivative.

In one aspect of the present invention, a compound wherein in said formula (I):
$R^1$ is selected from the group consisting of a hydrogen atom, a methyl group, an ethyl group, a propyl group, a butyl group, a pentyl group, a hexyl group, a heptyl group, an octyl group, a nonyl group, and a decyl group, and
$R^2$, $R^3$, and $R^4$ are a hydroxyl group
is preferred as the gallic acid derivative.

In one aspect of the present invention, a compound wherein in said formula (I):
$R^1$ is selected from the group consisting of a hydrogen atom, a methyl group, a propyl group, a butyl group, and an octyl group, and
$R^2$, $R^3$, and $R^4$ are a hydroxyl group
is preferred as the gallic acid derivative.

In one aspect of the present invention, those wherein the absorbance at around the excitation light wavelength of porphyrins 380-420 nm is modest are preferred as the gallic acid derivative.

Among gallic acids, a salt of gallic acid or a derivative thereof is not particularly limited as long as it is a pharmaceutically acceptable salt.

Among the above gallic acids, those preferred are alkyl esters such as a methyl gallate ester, a propyl gallate ester, a butyl gallate ester, and an octyl gallate ester. Especially, a methyl gallate ester, a propyl gallate ester, and an octyl gallate ester etc. can be exemplified as particularly preferable.

The above gallic acids are commercially available, and can also be manufactured by a well-known method such as chemical synthesis and extraction from plants. In addition, the gallic acids may be anhydrides or form hydrates or solvates, and gallic acids can also be used alone or in an appropriate combination of two or more.

Porphyrins refer to compounds having the basic skeleton of porphyrin. Examples of porphyrins include substances generally used as a porphyrin-based photosensitizer. Porphyrins produced by metabolism from ALAs can also be included as an example of porphyrins. Porphyrins generally have an absorption band at around 400-500 nm and at around 500-700 nm. For example, when PpIX receives an excitation light at the wavelength of 405 nm, it emits a red fluorescence having a peak at the wavelength of 635 nm.

Porphyrins that can be used in the present invention include those selected from the group consisting of protoporphyrin IX, uroporphyrin I, uroporphyrin III, coproporphyrin I, coproporphyrin III, heptacarboxylporphyrin I, heptacarboxylporphyrin III, hexacarboxylporphyrin I, hexacarboxylporphyrin pentacarboxylporphyrin I, pentacarboxylporphyrin isocoproporphyrin, harderoporphyrin, isoharderoporphyrin, mesoporphyrin IX, deuteroporphyrin IX, and pemptoporphyrin.

The details regarding the mechanism of how porphyrins are incorporated into tumor cells and accumulated are not clear. In one aspect of the present invention, porphyrins that emit fluorescence and have the nature of being accumulated in tumor cells are preferred.

Porphyrins are commercially available, and can also be manufactured by known methods.

A precursor of porphyrins herein refers to a substance that is metabolized in vivo to produce porphyrins. Porphyrin precursors include ALAs and the like.

In one aspect of the present invention, ALAs are preferred as the precursor of porphyrins. ALAs herein refer to ALA or a derivative thereof or salts thereof.

ALA herein means 5-aminolevulinic acid. ALA is also called δ-aminolevulinic acid, and is a type of amino acid. ALA is an endogenous substance in the body, and is known as a heme precursor. ALA is a common precursor of heme-based compounds, but it is known that in the case of cancer cells, heme is not produced even when ALA is administered, and a precursor for heme-based compounds, protoporphyrin IX (PpIX), is accumulated. Photodynamic diagnosis is possible because fluorescence is emitted when light is irradiated to the accumulated PpIX.

In the present invention, ALAs may be a compound shown by the following formula (II):

[Chemical Formula 5]

$$R^1\text{—NHCH}_2\text{COCH}_2\text{CH}_2\text{COOR}^2 \quad (II)$$

(wherein $R^1$ represents a hydrogen atom or an acyl group, and $R^2$ represents a hydrogen atom, a linear or branched alkyl group, a cycloalkyl group, an aryl group, or an aralkyl group)
or a salt thereof.

In the present invention, ALAs may be a compound wherein in said formula (II):
$R^1$ is selected from the group consisting of a hydrogen atom, an alkanoyl group having 1-8 carbons, and an aroyl group having 7-14 carbons, and
$R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

The acyl group of $R^1$ in said formula (II) can include a linear or branched alkanoyl group having 1-8 carbons such as a formyl, an acetyl, a propionyl, a butyryl, an isobutyryl, a valeryl, an isovaleryl, a pivaloyl, a hexanoyl, an octanoyl, and a benzylcarbonyl group, or an aroyl group having 7-14 carbons such as a benzoyl, a 1-naphthoyl, and a 2-naphthoyl group.

The alkyl group of $R^2$ in said formula (II) can include a linear or branched alkyl group having 1-8 carbons such as a methyl, an ethyl, a propyl, an isopropyl, a butyl, an isobutyl, a sec-butyl, a tert-butyl, a pentyl, an isopentyl, a neopentyl, a hexyl, a heptyl, and an octyl group.

The cycloalkyl group of $R^2$ in said formula (II) can include a cycloalkyl group having 3-8 carbons which may be saturated or have partially unsaturated bonds present, such as a cyclopropyl, a cyclobutyl, a cyclopentyl, a cyclohexyl, a cycloheptyl, a cyclooctyl, a cyclododecyl, and a 1-cyclohexenyl group.

The aryl group of $R^2$ in said formula (II) can include an aryl group having 6-14 carbons such as a phenyl, a naphthyl, an anthryl, and a phenanthryl group.

The aralkyl group of $R^2$ in said formula (II) can be exemplified with the same aryl groups as above as the aryl moiety and the same alkyl groups as above as the alkyl moiety, and can specifically include an aralkyl group having 7-15 carbons such as a benzyl, a phenethyl, a phenylpropyl, a phenylbutyl, a benzhydryl, a trityl, a naphthylmethyl, and a naphthylethyl group.

In the present invention, ALAs may be a compound wherein in said formula (II):

$R^1$ is selected from the group consisting of a hydrogen atom, a formyl group, an acetyl group, a propionyl group, and a butyryl group, and $R^2$ is selected from the group consisting of a hydrogen atom, a methyl, an ethyl, a propyl, a butyl, and a pentyl group.

In the present invention, ALAs may be a compound wherein in said formula (II):

$R^1$ is a hydrogen atom, and $R^2$ is selected from the group consisting of a hydrogen atom, a methyl, an ethyl, a propyl, a butyl, and a pentyl group.

In the present invention, ALAs may be a compound wherein in said formula (II):

$R^1$ is a hydrogen atom, and $R^2$ is a hydrogen atom.

Preferred ALA derivatives include compounds wherein the combination of the above $R^1$ and $R^2$ is each combination of (formyl and methyl), (acetyl and methyl), (propionyl and methyl), (butyryl and methyl), (formyl and ethyl), (acetyl and ethyl), (propionyl and ethyl), and (butyryl and ethyl).

Among ALAs, a salt of ALA or a derivative thereof can include a pharmaceutically acceptable acid addition salt, a metal salt, an ammonium salt, an organic amine addition salt, and the like. Acid addition salts can be exemplified by e.g. each of inorganic acid salts such as hydrochloride, hydrobromide, hydroiodide, phosphate, nitrate, and sulfate salts, and each of organic acid addition salts such as formate, acetate, propionate, toluenesulfate, succinate, oxalate, lactate, tartrate, glycolate, methanesulfonate, butyrate, valerate, citrate, fumarate, maleate, and malate salts. Metal salts can be exemplified by each of alkali metal salts such as lithium, sodium, and potassium salts, each of alkaline earth metal salts such as magnesium and calcium salts, and each of metal salts such as aluminum and zinc. Ammonium salts can be exemplified by alkyl ammonium salts such as an ammonium salt and a tetramethylammonium salt and the like. Organic amine salts can be exemplified by each of salts such as a triethylamine salt, a piperidine salt, a morpholine salt, and a toluidine salt. These salts can also be employed as a solution upon use.

Among the above ALAs, the most desirable are ALA and various esters such as an ALA methyl ester, an ALA ethyl ester, an ALA propyl ester, an ALA butyl ester, and an ALA pentyl ester, as well as hydrochloride, phosphate, and sulfate salts thereof. Among these, an ALA hydrochloride and an ALA phosphate can be exemplified as particularly preferable.

The above ALAs can be manufactured by e.g. a well-known method such as chemical synthesis, production by microorganisms, and production by enzymes. In addition, the above ALAs may also form a hydrate or a solvate, and ALAs can also be employed alone or in an appropriate combination of two or more.

Photobleaching herein refers to the occurrence of decrease in fluorescence of a photosensitizer. Inhibition of photobleaching refers to reducing the extent of decrease in fluorescence intensity that occurs within a certain amount of time after exciting a fluorescent substance, and includes not only complete decrease in fluorescence intensity but also suppression of decrease in fluorescence intensity. Accordingly, a photobleaching inhibitor can also be referred to as a photobleaching suppressor.

Photodynamic diagnosis (also referred to herein as "PDD") is a method of diagnosing the area/range of the lesion site of a tumor etc. that utilizes the nature of a photosensitizer such as porphyrins of being incorporated into a tumor etc. and accumulated, in which a photosensitizer or a precursor thereof is administered to a subject and excitation light is irradiated to thereby detect the fluorescence emitted by the photosensitizer. For example, it is known that PpIX can be employed for tumor diagnosis by photodynamic diagnosis by virtue of the fact that it emits a red fluorescence having a peak at the wavelength of 635 nm when it receives an excitation light at the wavelength of 405 nm, and applications in diagnosis of brain tumor or bladder cancer etc. are expected.

In photodynamic diagnosis, the wavelengths of the excitation light and the fluorescence of the photosensitizer suitable for each compound can be appropriately selected based on the measurement results of the absorption spectrum and the fluorescence spectrum etc. of each porphyrin.

For example, as the light to be irradiated from the excitation light irradiation means for PpIX, light at a wavelength that enables observation of red fluorescence intrinsic to PpIX by exciting the PpIX is preferred, which can include a violet wavelength close to the ultraviolet light that belongs to the absorption peak of PpIX belonging to the so-called Soret band, specifically an excitation light at a wavelength of 380 nm-420 nm, preferably 400-410 nm, particularly preferably 403-407 nm, and above all 405 nm. This can also be measured and appropriately determined for other porphyrins.

Means for performing photodynamic diagnosis can be exemplified with a means for irradiating the excitation light for porphyrins, a means for detecting fluorescence intrinsic for porphyrins in excited state, or an integrated means thereof.

Those well-known can be used as the light source for irradiating the above excitation light, and can include a laserbeam such as a violet LED, preferably a flashlight-type violet LED, or a semiconductor laser, although a violet LED, among them a flashlight-type violet LED, or a violet semiconductor diode which will allow a compact device and be advantageous in regards to cost or portability can be preferably exemplified.

Means for detecting the above fluorescence can include not only a detection means by naked eye or a detection means by a CCD camera but also a detection means employing an appliance such as a colposcope.

The integrated photodynamic diagnostic means between the excitation light irradiation means and the red fluorescence detection means can include a light source and a thin optical fiber for measurement, wherein the light source for the excitation light is preferably a semiconductor laser light source that has strong irradiance in order to enable detection of porphyrins even in tumors microscopically scattered in the living tissue of test subject and has a narrow irradiation area in order to enable precise auto-detection, and preferably has an excitation light optical guiding part that optically guides the excitation light and emits it from one end to the exterior. The excitation light optical guiding part can specifically include a thin optical fiber. A semiconducting mixed crystal such as InGaN can be employed as the element employed for the light source, and a violet light can be oscillated by changing the compounding ratio of InGaN. Specifically, a compact laser diode having a diameter of about 5.6 mm can be suitably exemplified. A 4-laser output port from the laser diode and a spectrum measuring port can be exemplified with a device that is about the size of a desktop PC linked with a built-in high sensitivity spectroscope. In addition, a thin optical fiber for measurement is employed in the photoreceiving step of receiving the fluorescence light emitted from PpIX excited by said excitation light, wherein the thin optical fiber for measurement is integrated with said thin optical fiber for light source, and the received fluorescence light is optically guided to a detector to determine the porphyrins accumulation site.

In the present invention, the lesion site to be the target of photodynamic diagnosis includes a tumor site, a precancerous lesion, and the like. In one aspect of the present invention, the lesion site as the target of diagnosis is preferably a tumor.

In one aspect of the present invention, the tumor to be the target of photodynamic diagnosis is a malignant or a non-malignant tumor. Malignant tumors show malignancy such as by invasively proliferating and metastasizing. Accounting for a large part among malignant tumors are cancers derived from epithelial cells, and others include sarcomas, lymphomas, or leukemias. A non-malignant tumor indicates a disease other than malignant tumors, e.g. a benign disease, but it does not necessarily mean that therapy is easy.

Tumor tissues include, but are not particularly limited to, brain, nasal meatus, nasal cavity, trachea, bronchial tube, oral cavity, pharynx, esophagus, stomach, breast, colon rectum, lung, ovary, central nervous system, liver, bladder, urethra, urinary duct, pancreas, cervical duct, peritoneal cavity, anal canal, uterine cervix, and the like.

Examples of the administration route of the photodynamic diagnostic agent of the present invention can include oral administration including sublingual administration, inhalation administration, intravenous administration including infusion, transdermal administration by patch and the like, and parenteral administration such as administration by forced enteral nutrition method employing a suppository, a nasogastric tube, a nasointestinal tube, a gastrostomy tube, or an enterostomy tube, although oral administration is common. In the present invention, the precursor of porphyrins and the gallic acid can have different administration routes.

In addition to said administration route, the photobleaching inhibitor of the present invention can also be directly administered to a lesion site such as in the bladder. In one aspect of the present invention, the precursor of porphyrins is preferably orally administered to directly administer the photobleaching agent to the lesion site.

The dosage form of the photodynamic diagnostic agent of the present invention can be appropriately determined according to the above administration route, examples of which can include an injection, an infusion, a tablet, a capsule, fine granules, powders, liquids, a liquor dissolved in e.g. a syrup, a poultice, and a suppository. In the present invention, the precursor of porphyrins and the gallic acid can be in different dosage forms.

In order to prepare the photodynamic diagnostic agent of the present invention, a carrier, an excipient, a diluent, an additive, a disintegrant, a binder, a coating, a lubricant, a glider, a lubricant, a flavoring agent, a sweetening agent, a solubilizer, a solvent, a gelling agent, a nutrient and the like that may be pharmacologically acceptable can be added as necessary, specific examples of which can be water, saline, animal fat and oil, vegetable oil, lactose, starch, gelatin, crystalline cellulose, gum, talc, magnesium stearate, hydroxypropylcellulose, polyalkylene glycol, polyvinyl alcohol, and glycerin. When the photodynamic diagnostic agent of the present invention is to be prepared as an aqueous solution, attention must be paid so that the aqueous solution will not become alkaline in order to prevent degradation of ALAs. In the case it becomes alkaline, degradation can also be prevented by removing oxygen.

The amount, the frequency, and the duration and the photodynamic diagnostic agent of the present invention are not particularly limited. They can be appropriately optimized according to the age, weight, and symptoms etc. of the subject who will be utilizing the photodynamic diagnostic agent.

In one aspect of the present invention, examples of the preferred dosage for the precursor of porphyrins (such as ALAs) can include, e.g., 0.0006 mmol-6 mmol, preferably 0.006 mmol-0.6 mmol, and more preferably 0.06 mmol-0.3 mmol per 1 kg of body weight of ALA equivalent.

In one aspect of the present invention, examples of the preferred dosage for gallic acids can include, e.g., 0.00006 mmol-600 mmol, preferably 0.0006 mmol-60 mmol, and more preferably 0.006 mmol-30 mmol per 1 kg of body weight of propyl gallate equivalent. The preferred dosage can be appropriately determined according to the administration route. For example, depending on the administration route, e.g. in the case of a direct intravesical administration, administration can be so that the final intravesical concentration of the gallic acid is 0.01-20%, preferably 0.1%-10%, and more preferably 0.5%-10%.

The preferred dosage can also be calculated when employing other precursor of porphyrins, gallic acids, and ALAs by calculating the molar equivalency. Naturally, the above preferred dosage range is merely an exemplification and is not limiting.

In one aspect of the present invention, the proportion of the dosages between the precursor of porphyrins (such as ALAs) and the gallic acid can be appropriately optimized by those skilled in the art in light of the extent of the photobleaching effect by gallic acids.

In one aspect of the present invention, the preferred proportion of the dosages between the precursor of porphyrins (such as ALAs) and the gallic acid can include 0.01-10000 folds, preferably 0.1-1000 folds, more preferably, 1-1000 folds of the gallic acids dosage to the ALAs dosage in molar ratio. Naturally, the above dosage proportion range is merely an exemplification and is not limiting.

The photodynamic diagnostic agent containing the precursor of porphyrins and the gallic acid can be administered as a composition of the precursor of porphyrins and the gallic acid or each alone. When administering each alone, the gallic acid can be administered before, simultaneously, or after the administration of the precursor of porphyrins. In the case of simultaneous administration, the administration may not need to be strictly simultaneous but without a substantial interval between the two.

In regards to the time interval between the administration of the photodynamic diagnostic agent characterized in combining the precursor of porphyrins (such as ALAs) and the gallic acid and diagnosis, the photodynamic diagnosis is preferably carried out 30 minutes-8 hours, preferably 1 hour-6 hours, more preferably 2 hours-5 hours, and further preferably 3.5 hours-4.5 hours post administration of the precursor of porphyrins (such as ALAs) so that the difference in porphyrins concentration between the lesion site tissue and normal tissue will be large.

The administration of gallic acids may be at any of before administration of the precursor of porphyrins (such as ALAs), simultaneously with the administration of the precursor of porphyrins (such as ALAs), or after the administration of the precursor of porphyrins (such as ALAs). Moreover, the precursor of porphyrins (such as ALAs) and the gallic acid may have different administration routes. In one aspect of the present invention, it is preferred that the precursor of porphyrins is orally administered and the gallic acid is directly administered to the lesion site.

The photodynamic diagnostic agent of the present invention can also be used in combination with other existing photodynamic diagnostic agents and/or other photobleaching inhibitors. Examples of existing photodynamic diagnostic agents include Photofrin™, Laserphyrin™, indocyanine green, and the like. As other photobleaching inhibitors, gallic acids found in the present invention as well as other photobleaching inhibitors may be combined. An additive or in some cases a synergetic effect can be expected by combination use.

The method for detecting the porphyrins accumulation site according to the present invention can be performed by e.g. a method comprising the following steps:

a step of irradiating the excitation light for porphyrins to a subject who has been administered in advance a precursor of porphyrins and a gallic acid at simultaneous or different times, and a step of detecting the fluorescence of porphyrins.

Said subject here is typically a human, but non-human animals such as pet animals, experimental animals, and farm animals are also included.

The porphyrins accumulation site here includes mainly tumors or precancerous lesions and the like. A typical example of said precursor of porphyrins is said ALAs.

The photodynamic diagnostic method according to the present invention can be performed by e.g. a method comprising the following steps (1)-(4):

(1) a step of administering a precursor of porphyrins and the gallic acid to a subject at simultaneous or different times, (2) a step of irradiating the excitation light for porphyrins to the subject, (3) a step of detecting the fluorescence of porphyrins, and (4) a step of deciding the porphyrins accumulation site based on the detected fluorescence of porphyrins and determining the range of lesion site.

Said subject here is typically a human, but non-human animals such as pet animals, experimental animals, and farm animals are also included.

In addition, said lesion site is typically a tumor. A typical example of said precursor of porphyrins is said ALAs.

The terms used herein are employed to describe particular embodiments, and do not intend to limit the invention.

In addition, unless the content clearly indicates to be understood otherwise, the term "comprising" as used herein intends the presence of the described items (such as components, steps, elements, and numbers), does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. Unless explicitly defined otherwise, the terms used herein are to be construed as having meanings consistent with meanings in the present specification and related technical fields, and are not to be construed as idealized or excessively formal meanings.

The present invention will now be described in further detail with reference to Examples. However, the present invention can be embodied by various aspects, shall not be construed as being limited to the Examples described herein.

EXAMPLES

Example 1

Measurement of Photobleaching Inhibitory Effect for PpIX Metabolized and Produced from ALAS when ALAS and Gallic Acids or Other Reductants were Incorporated into Cells MKN45 cells were seeded in a 35 mm dish at $0.5 \times 10^6$ cells, and the culture medium on the 35 mm dish was 2 mL. Ten μL of 0.2 M ALA hydrochloride (5-aminolevulinic acid hydrochloride) solution was added to the 2 mL of culture medium in the 35 mm dish to achieve the final concentration of ALA in the culture medium at 1 mM. This 35 mm dish was cultured in a 5% $CO_2$ incubator at 37° C. for 24 hours. The cells were then washed with 1 ml of PBS, 1 mL of each of the following reductant solutions (dissolved in 50% glycerol PBS solution) were added on ice, the cells were immediately scraped off with a cell scraper, and the cells were suspended by pipetting. The fluorescence intensity at 635 nm of each of these cell suspensions under the excitation light at 400 nm was measured. The fluorescence intensity was measured from 0 seconds post irradiation of excitation light for every 10 seconds until 180 seconds post irradiation. Not limited to Example 1, the measurement of fluorescence intensity was performed with irradiation of the excitation light even after the 0 seconds post irradiation of excitation light.

The following were employed at the following final concentrations as each reductant:

Paraphenylenediamine (hereinafter abbreviated as "PPD"): 0.5% n-propyl gallate (hereinafter abbreviated as "NPG"): 2%

1-4-diazabicyclo[2.2.2]-octane (hereinafter abbreviated as "DABCO"): 5%

Prolong Gold™: approximately 1% as the active ingredient sodium azide

Since Prolong Gold (an anti-fade agent from Invitrogen) was sold as a solution containing approximately 1% of sodium azide, it was added directly as the commercially available solution without employing 50% glycerol/PBS to carry out the investigation.

The results of Example 1 are shown in FIG. 1. Among the various reductants, when propyl gallate was employed, superior photobleaching inhibitory effect was observed, given that fluorescence intensity was maintained at about half of the fluorescence intensity at 0 seconds post irradiation of excitation light of the control even after 180 seconds post irradiation of excitation light. On the other hand, when DABCO was employed, the photobleaching inhibitory effect was observed to be insufficient. In addition, when PPD was employed, the fluorescence intensity at 0 seconds post irradiation of excitation light itself was markedly reduced, and a state of high fluorescence intensity as with NPG could not be maintained. Moreover, when Prolong Gold commercially marketed as an Anti-fading agent was employed, the fluorescence intensity was reduced more than the control, and thus a photobleaching inhibitory effect was not observed.

Example 2

Measurement of Photobleaching Inhibitory Effect for PpIX Metabolized and Produced from ALAs when ALAs and Other Reductants were Incorporated into Cells Photobleaching suppression effect for PpIX was measured for other reductants. The following were employed as the reductants. Each reductant solution was prepared by the following method and each of the prepared solutions was used as sample solvents for photobleaching measuring.

Solution supplemented with 5 μL of ascorbic acid (solvent: milli Q, concentration of supplemented solution: 100 mM) was added to 1 mL of PBS to prepare an ascorbic acid solution having a final concentration of 500 μM.

Solution supplemented with 5 μL of tocopherol (solvent: DMSO, concentration of supplemented solution: 100 mM) was added to 1 mL of PBS to prepare a tocopherol solution having a final concentration of 500 μM.

Solution supplemented with 5 μL of lutein (solvent: DMSO, concentration of supplemented solution: 2 mM) was added to 1 mL of PBS to prepare a lutein solution having a final concentration of 10 μM.

MKN45 cells were seeded in a 35 mm dish at $0.5 \times 10^6$ cells, and the culture medium on the 35 mm dish was 2 mL. Ten μL of 0.2 M ALA hydrochloride (5-aminolevulinic acid hydrochloride) solution was added to the 2 mL of culture medium in the 35 min dish to achieve the final concentration of ALA in the culture medium at 1 mM. This 35 mm dish was cultured in a 5% $CO_2$ incubator at 37° C. for 24 hours. The cells were then washed with 1 ml of PBS, and then 1 mL of each of the reductant solutions prepared as above were added, the cells were immediately scraped off with a cell scraper, and the cells were suspended by pipetting. The fluorescence intensity at 635 nm of each of these cell suspensions under the excitation light at 400 nm was measured. The fluorescence intensity was measured from 0 seconds post irradiation of excitation light for every 10 seconds until 180 seconds post irradiation. The measurement of fluorescence intensity was performed with irradiation of the excitation light even after the 0 seconds post irradiation of excitation light.

Figure 2:
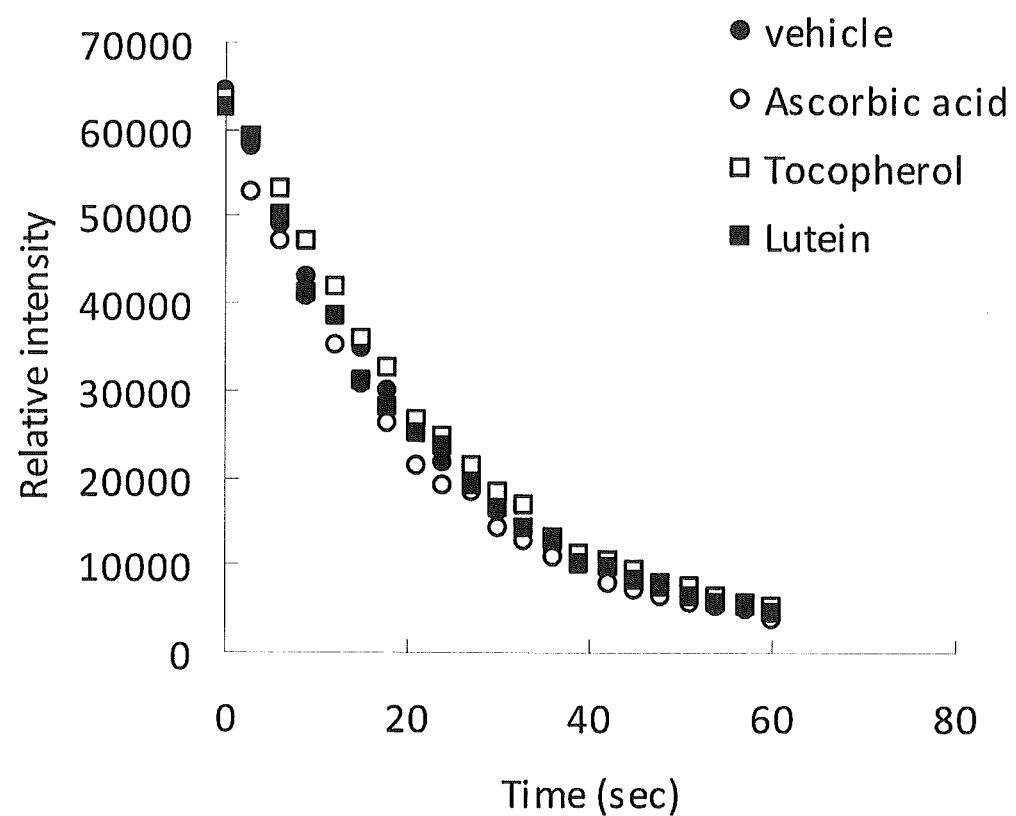
FIG. 2 shows the plot of the fluorescence intensity for every 10 seconds from 0 to 180 seconds post irradiation of excitation light in regards to the transition of fluorescence intensity of PpIX in the presence of each reductant when ALAs and a reductant (ascorbic acid, α-tocopherol, or lutein) were incorporated into cells.

The results of Example 2 are shown in FIG. 2. In the presence of any of ascorbic acid, tocopherol, and lutein, the fluorescence intensity of PpIX was observed to rapidly reduce similarly to the control. Accordingly, it was observed that these reductants also do not have the effect of inhibiting photobleaching of PpIX.

Example 3

In a method similar to Example 1, 1 mL of 1% n-propyl gallic acid (NPG) solution was added, and the intensity of the excitation light was altered to 0.1 mA, 0.2 mA, 0.3 mA, and 0.4 mA to measure the fluorescence intensity.

Figure 3:
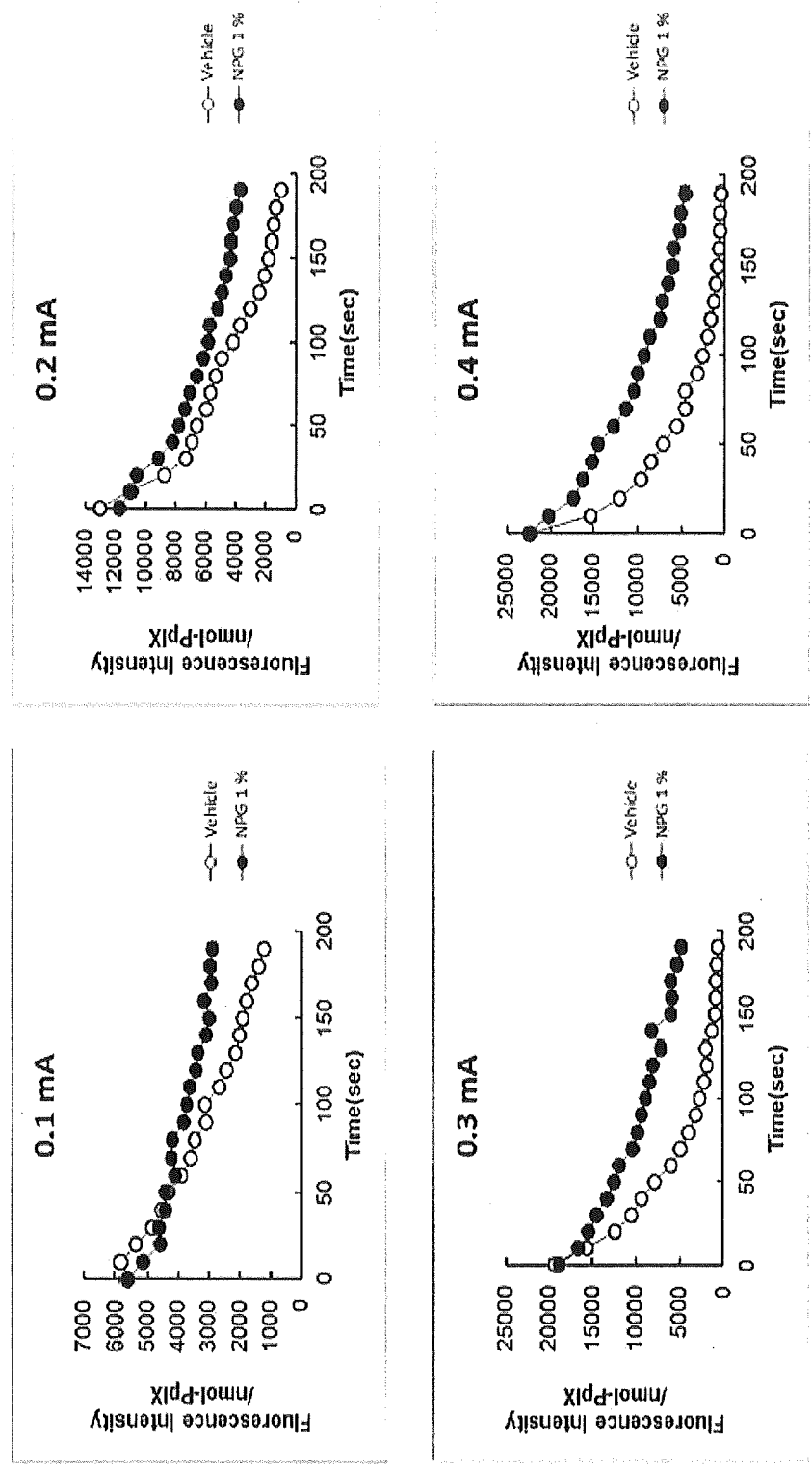
FIG. 3 shows the plot of the fluorescence intensity for every 10 seconds from 0 to 180 seconds post irradiation of excitation light in regards to the transition of fluorescence intensity of PpIX in the presence or absence of propyl gallate when ALAs and propyl gallate were incorporated into cells.

The results of Example 3 are shown in FIG. 3. In the Figures, the description "vehicle" shows the fluorescence intensity when 1 mL of 50% glycerol PBS solution was added as a control instead of 1% n-propyl gallic acid (NPG) solution.

The half-life calculated from these measurement results are shown in Table 1.

TABLE 1

| Current Intensity | Half-life (sec) | |
| --- | --- | --- |
| (mA) | Vehicle | NPG 1% |
| 0.1 | 115 | 195 |
| 0.2 | 50 | 95 |
| 0.3 | 35 | 85 |
| 0.4 | 25 | 75 |

There is a tendency that the degradation of PpIX will advance and fluorescence will largely decrease at an earlier timing when strong excitation light is irradiated. It was observed that by adding NPG, the half-life was prolonged by three folds from 25 seconds to 75 seconds when the intensity of the excitation light was 0.4 mA.

Figure 4:
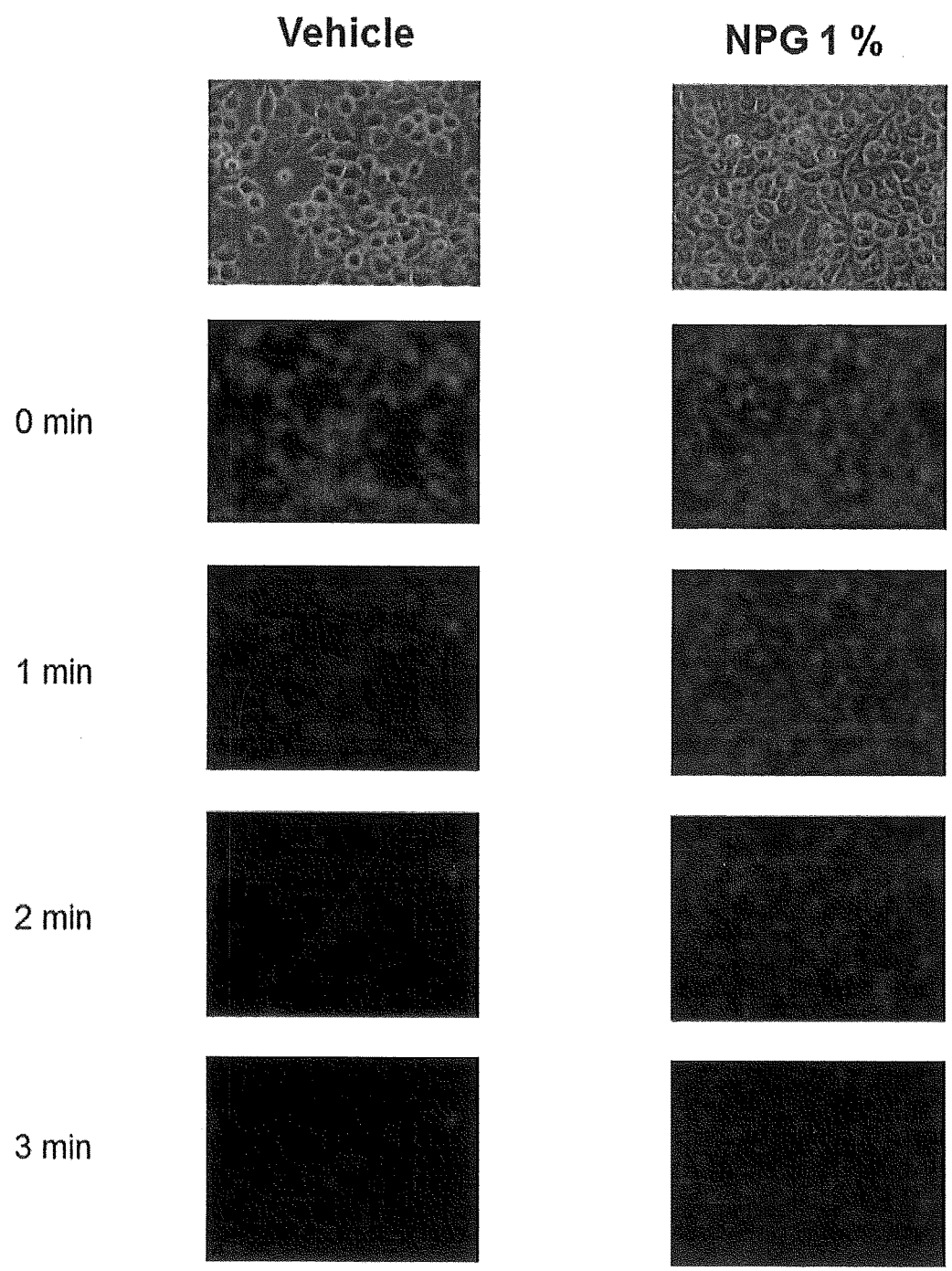
FIG. 4 shows the material image of cells (top) as well as pictures of said cells photographed with a fluorescence microscope at 0, 1, 2, and 3 minutes post irradiation of excitation light, when ALAs and propyl gallate were incorporated into cells. "Vehicle" in the Figure shows cells in the absence of propyl gallate (as a control).

Photographic images by a fluorescence microscope for the results of Example 3 are shown in FIG. 4. It was observed that fluorescence was maintained for a longer duration when 1% of NPG was added.

Example 4

Measurement of Photobleaching Inhibitory Effect for Porphyrins by Each Alkyl Gallate in Solution The photobleaching inhibitory effect for porphyrins by gallic acids was measured with the following procedure. Methyl gallate (MeG, from Wako, Cat. No. 134-09812), butyl gallate (BuG, from Wako, Cat. No. 322-67472), n-propyl gallate (PrG, from Wako, Cat. No. 162-06832), and octyl gallate (OcG, from Wako, Cat. No. 322-56482) were employed as gallic acids. The gallic acids employed here are all compounds having a linear alkyl.

(1) In order to prepare 50 mM solutions of each alkyl gallate, 0.3 mmol of each alkyl gallate was placed in a 15 mL tube, and 6 mL of 50% glycerol PBS solution (a mixture of glycerol and PBS at a proportion of 1:1, hereinafter may be notated as "Gly+PBS" or "Gly+PBS solution") or DMSO was added and dissolved.

Because octyl gallate could not be dissolved in the Gly+PBS solution, DMSO solutions of each alkyl gallate were also prepared. Butyl gallate was able to dissolve in Gly+PBS solution and DMSO, but both solutions became yellow-colored solutions.

(2) Measurement of the absorption spectrum at 350 nm-750 nm was performed with 1000 μL of each alkyl gallate solution prepared in (1).

Among the above four types of each alkyl gallate solution, only butyl gallate was found to have absorbance at around 400 nm. Since the fluorescent substance protoporphyrin IX (PpIX) has a sharp absorbance at around 400 nm, and a light at around 400 nm is employed as the excitation light, it was deemed possible that excitation of PpIX could be inhibited when employing butyl gallate.

(3) After dispensing 990 μL of alkyl gallate into a 2 mL vial, 10 μL of 100 μM PpIX was added (final concentration of PpIX at 1 μM).

(4) Measurement of the fluorescence spectrum was performed for each alkyl gallate+PpIX solution prepared in (3) with a simplified fluorescence measurement device. LED was employed as the light source, the wavelength of the excitation light employed was 402 nm, the output current was set at 0.4 mA, and the measurement interval was every 10 seconds until 180 seconds for measurement.

The measurement results for Example 4 when a Gly+PBS solution was employed as the solvent for gallic acids are shown in FIG. 5-FIG. 8. Each Figure will be described below. The vertical axis in FIGS. 5-13 is described as relative intensity this shows a relative value against the fluorescence intensity measured as a blank by sealing the fiber connection part so that no light will come in.

Figure 5:
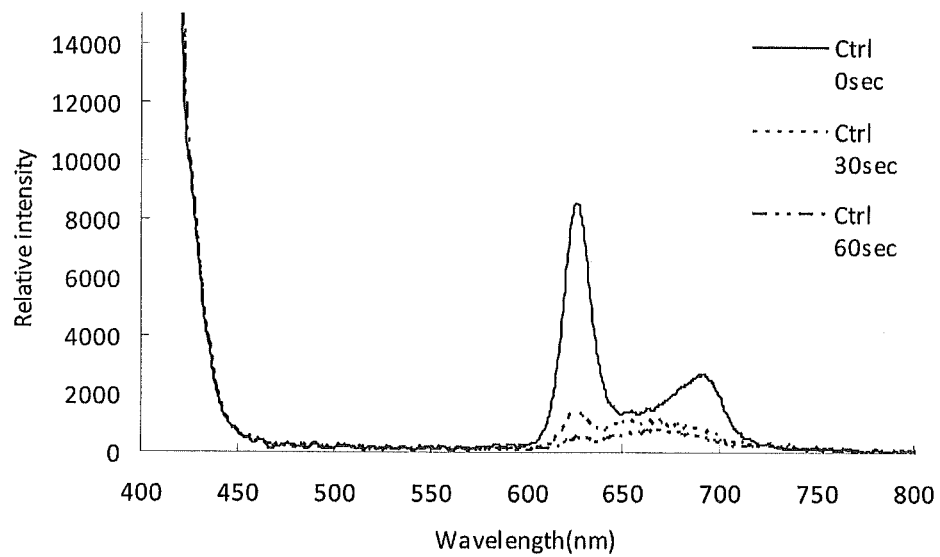
FIG. 5 shows the fluorescence spectrum of PpIX in a Gly+PBS solution which does not comprise any gallic acid (as a control).

As a control, the fluorescence spectrum of PpIX in a Gly+PBS solution which does not comprise any gallic acid is shown in FIG. 5. A strong fluorescence having a peak at around 627 nm was measured with PpIX. Relative to the fluorescence intensity at seconds post irradiation of excitation light, fluorescence intensity was decreased to about one fifth a mere 30 seconds later and to about one tenth 60 seconds later.

Figure 6:
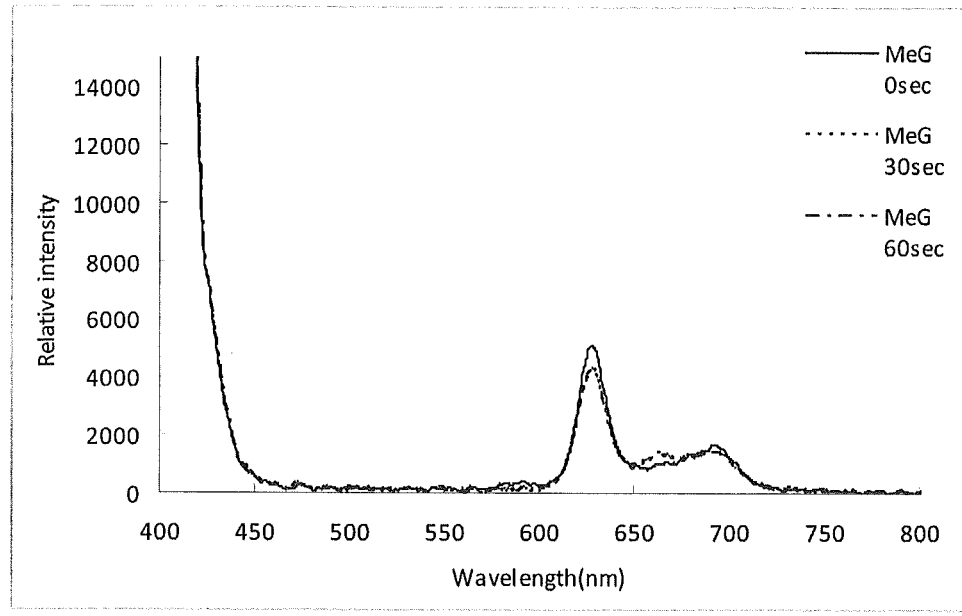
FIG. 6 shows the fluorescence spectrum of PpIX in a Gly+PBS solution comprising methyl gallate as the gallic acid.
Figure 7:
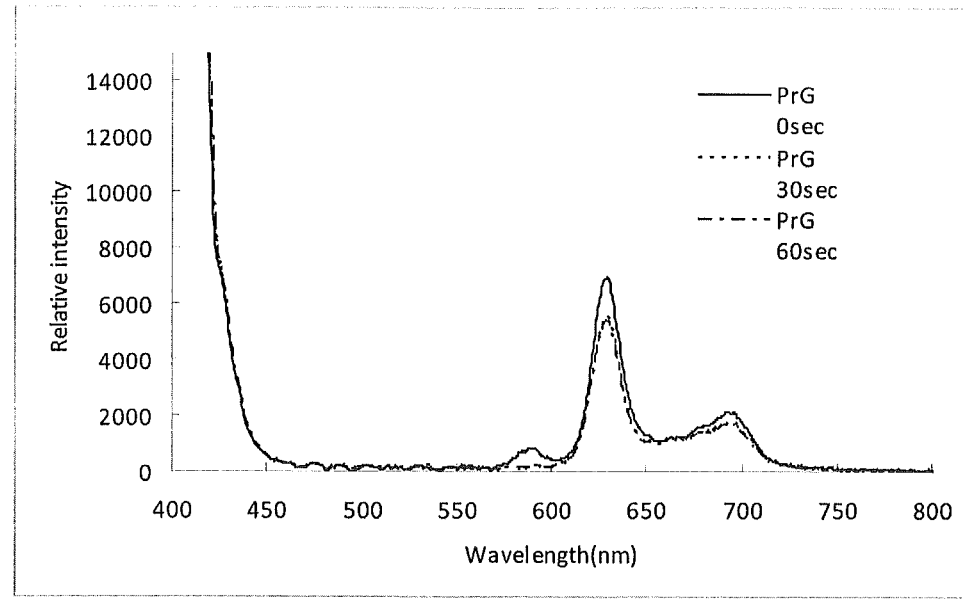
FIG. 7 shows the fluorescence spectrum of PpIX in a Gly+PBS solution comprising propyl gallate as the gallic acid.
Figure 8:
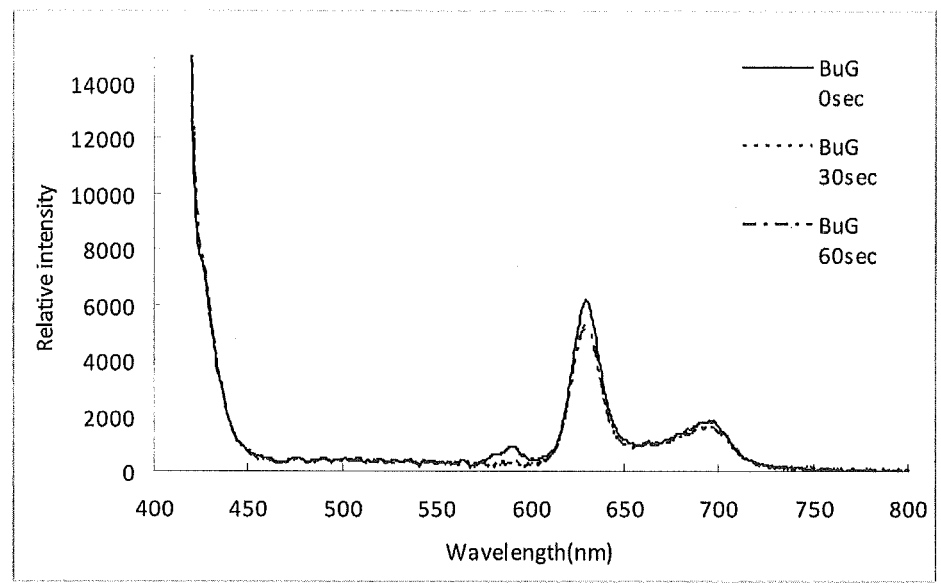
FIG. 8 shows the fluorescence spectrum of PpIX in a Gly+PBS solution comprising butyl gallate as the gallic acid.

In regards to the effect of each gallic acid, the fluorescence spectrum of PpIX in a Gly+PBS solution comprising methyl gallate, propyl gallate, or butyl gallate are shown in FIG. 6, 7, or 8, respectively. Relative to the fluorescence intensity at 0 seconds post irradiation of excitation light, the fluorescence intensity of PpIX was only modestly reduced even after 30 seconds and after 60 seconds, and photobleaching of PpIX could be suppressed.

The measurement results for Example 4 when a DMSO solution was employed as the solvent for gallic acids are shown in FIG. 9-FIG. 13. Each Figure will be described below.

Figure 9:
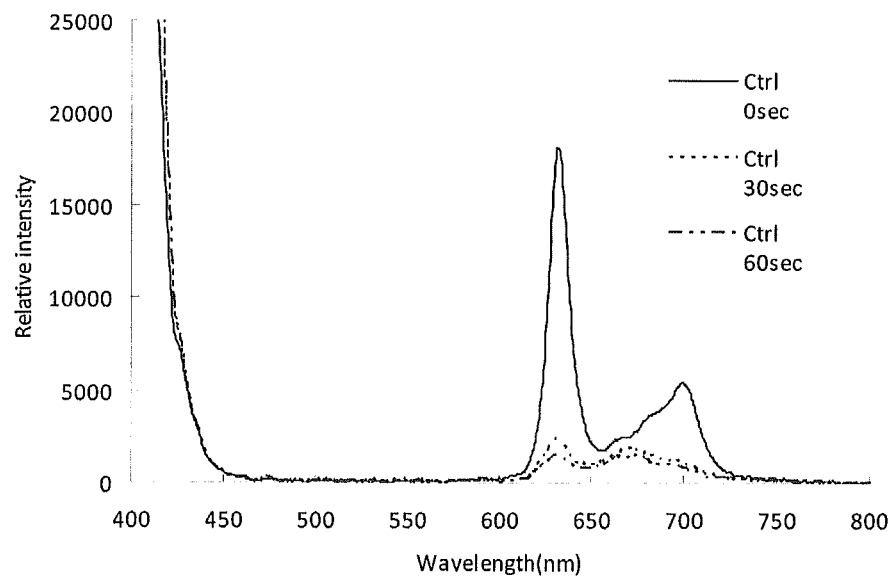
FIG. 9 shows the fluorescence spectrum of PpIX in a DMSO solution which does not comprise any gallic acid (as a control).
Figure 10:
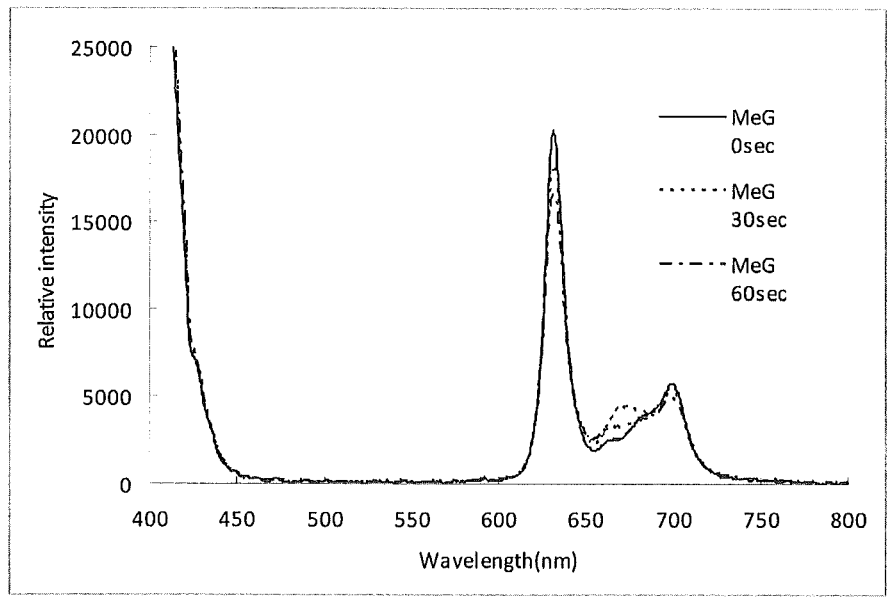
FIG. 10 shows the fluorescence spectrum of PpIX in a DMSO solution comprising methyl gallate as the gallic acid.
Figure 11:
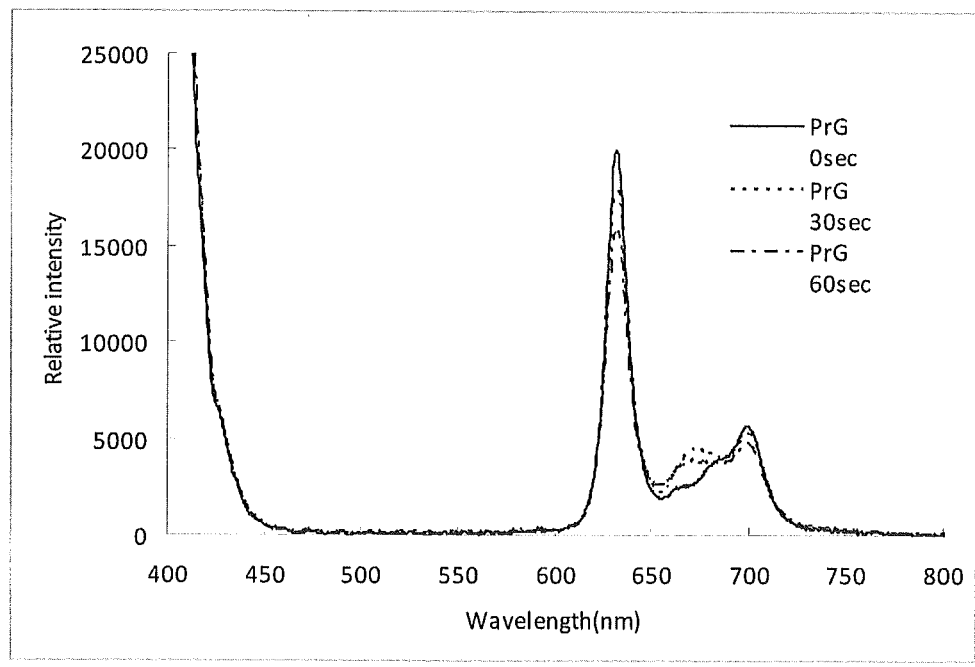
FIG. 11 shows the fluorescence spectrum of PpIX in a DMSO solution comprising propyl gallate as the gallic acid.
Figure 12:
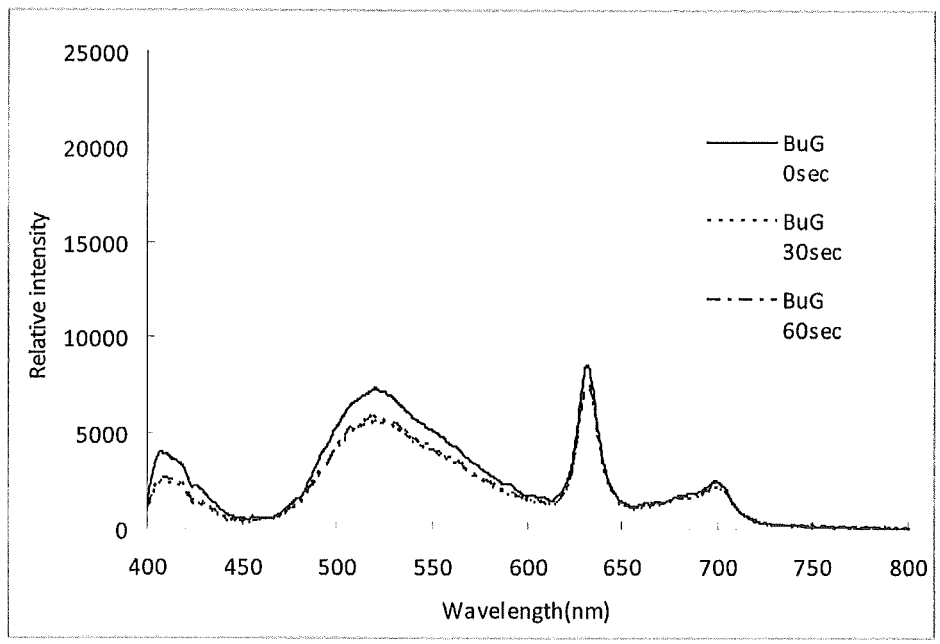
FIG. 12 shows the fluorescence spectrum of PpIX in a DMSO solution comprising butyl gallate as the gallic acid.
Figure 13:
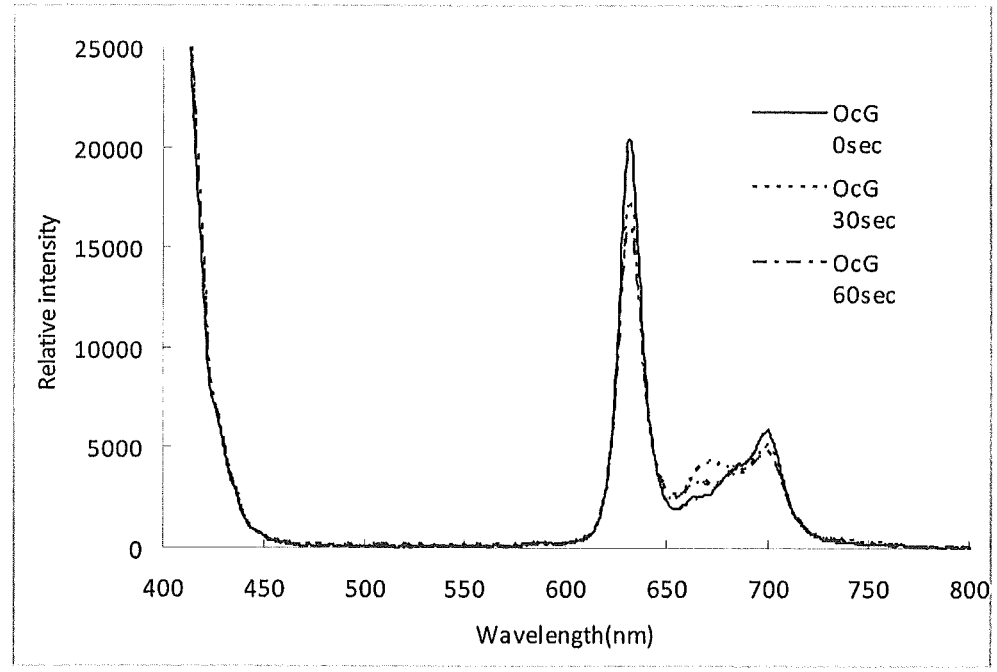
FIG. 13 shows the fluorescence spectrum of PpIX in a DMSO solution comprising octyl gallate as the gallic acid.

As a control, the fluorescence spectrum of PpIX in a DMSO solution which does not comprise any gallic acid is shown in FIG. 9. A strong fluorescence having a peak at around 632 nm was measured with PpIX. Similarly to when a Gly+PBS solution was employed as the solvent, when DMSO was employed as the solvent for gallic acids, fluorescence intensity was also decreased to about one fifth a mere 30 seconds later and to about one tenth 60 seconds later relative to the fluorescence intensity at 0 seconds post irradiation of excitation light.

In regards to the effect of each gallic acid, the fluorescence spectrum of PpIX in a DMSO solution comprising methyl gallate, propyl gallate, butyl gallate, or octyl gallate are shown in FIG. 10, 11, 12, or 13, respectively. Relative to the fluorescence intensity of PpIX at 0 seconds post irradiation of excitation light, the fluorescence intensity of PpIX was only modestly reduced even after 30 seconds and after 60 seconds when any of the alkyl gallates were employed, and photobleaching of PpIX could be suppressed. The fluorescence detected at around 500-550 nm in the presence of butyl gallate is thought to be derived from butyl gallate.

Figure 14:
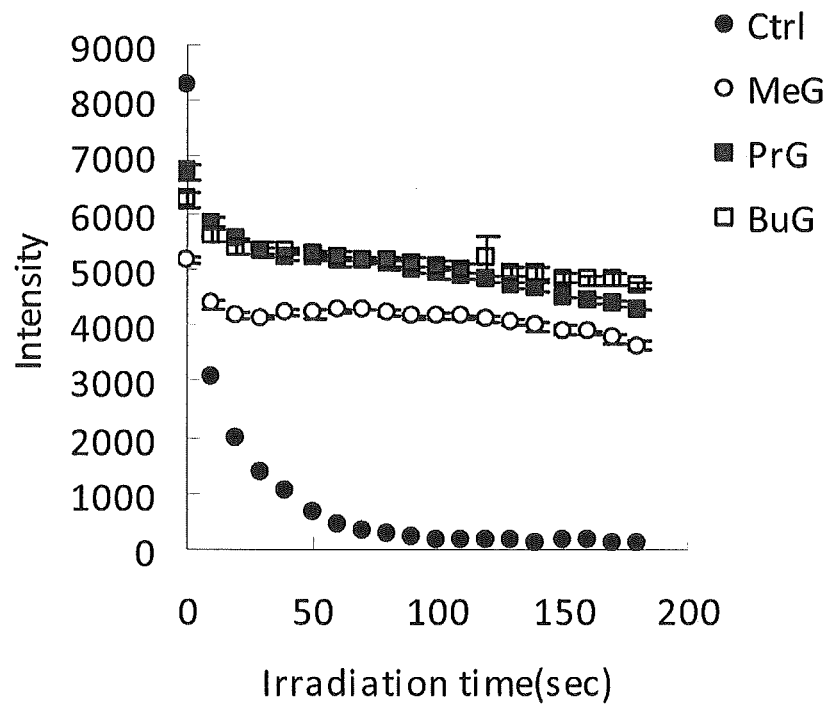
FIG. 14 shows the plot of the fluorescence intensity for every 10 seconds from 0 to 180 seconds post irradiation of excitation light in regards to the transition of fluorescence intensity of PpIX in the presence of each alkyl gallate when a Gly+PBS solution was employed.
Figure 15:
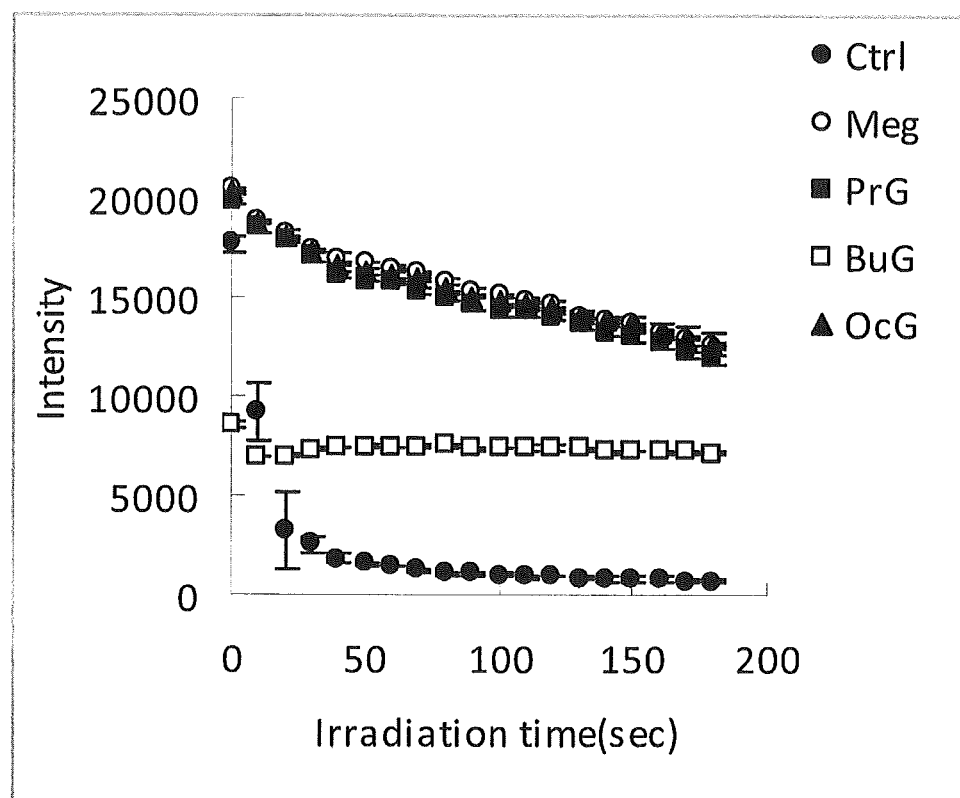
FIG. 15 shows the plot of the fluorescence intensity for every 10 seconds from 0 to 180 seconds post irradiation of excitation light in regards to the transition of fluorescence intensity of PpIX in the presence of each alkyl gallate when a DMSO solution was employed.

For the results of the above Example 4, the plot of the fluorescence intensity for every 10 seconds from 0 to 180 seconds post irradiation of excitation light (excitation light output all at 0.4 mA) so that the transition of the fluorescence intensity of PpIX for every 10 seconds in the presence and absence of each alkyl gallate is seen, is shown in FIGS. 14 and 15. Each Figure will be described below.

Figure 16:
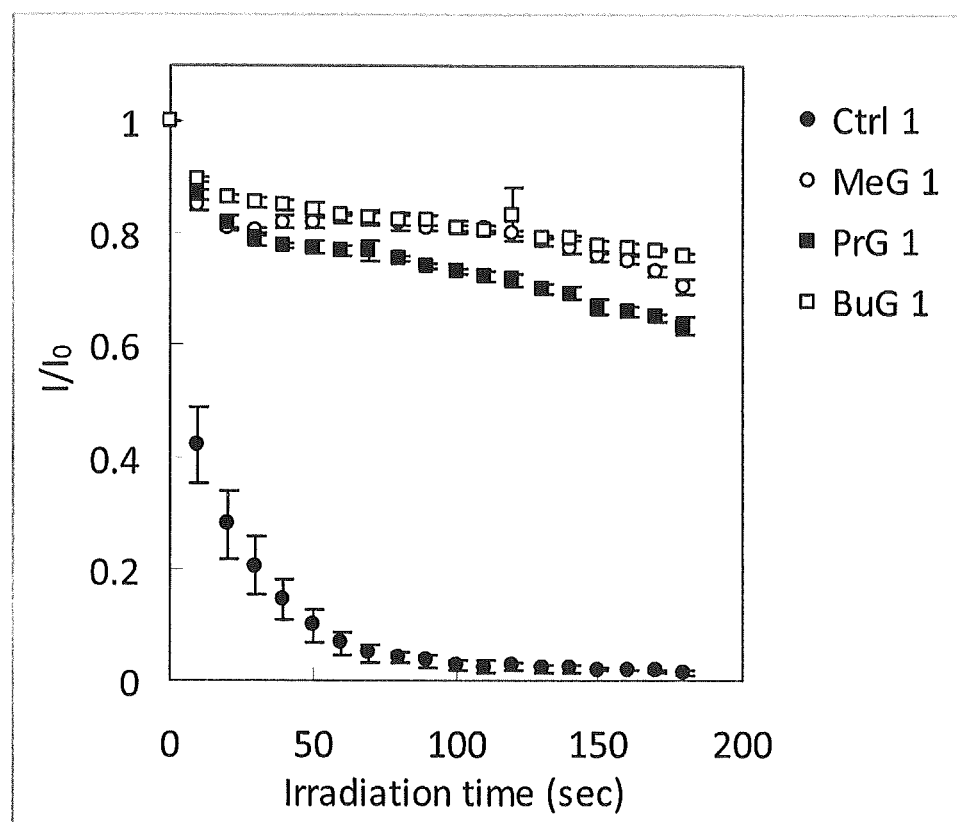
FIG. 16 shows the plot of the relative value when the fluorescence intensity immediately post irradiation was set as 1 in regards to the transition of fluorescence intensity of PpIX in the presence of each alkyl gallate when a Gly+PBS solution was employed.

The transition of fluorescence intensity at fluorescent wavelength 627 nm when a Gly+PBS solution was employed as the solvent for gallic acids is shown in FIG. 15. In addition, the transition of fluorescence intensity at fluorescent wavelength 632 nm when a DMSO solution was employed as the solvent for gallic acids is shown in FIG. 16. In the absence of alkyl gallate (control), the fluorescence intensity was reduced to one tenth or less already at 60 seconds post irradiation of excitation light and significant photobleaching had occurred, whereas in the presence of each alkyl gallate, the fluorescence intensity was only modestly reduced even at 60 seconds, 120 seconds, and 180 seconds post irradiation of excitation light. Accordingly, it was observed that each alkyl gallate had the effect of suppressing photobleaching of PpIX.

Figure 17:
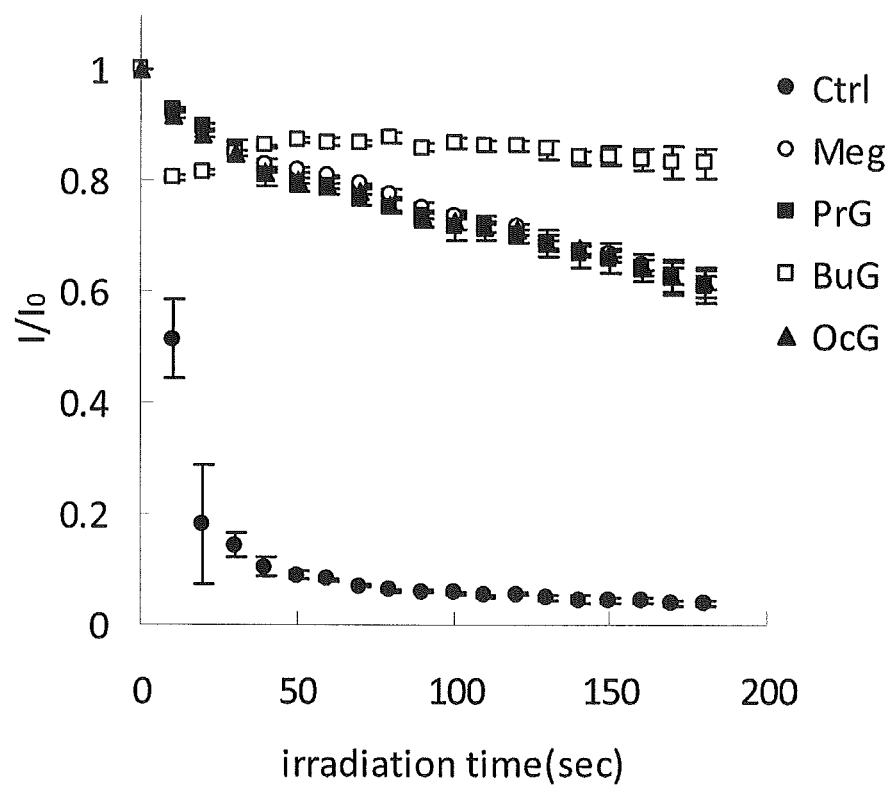
FIG. 17 shows the plot of the relative value when the fluorescence intensity immediately post irradiation was set as 1 in regards to the transition of fluorescence intensity of PpIX in the presence of each alkyl gallate when a DMSO solution was employed.

For each of the plots above in FIG. 14 and FIG. 15 when a Gly+PBS solution and a DMSO solution was employed as the solvent for gallic acid, the relative fluorescence intensity was calculated by setting the fluorescence intensity immediately post irradiation (0 seconds later) as 1, and the transition of fluorescence intensity of PpIX was plotted with the calculated relative intensity as the vertical axis as shown in FIG. 16 and FIG. 17, respectively. This transition of relative fluorescence intensity was treated as a pseudo-first-order reaction to determine the half-life, and shown in Table 2 and Table 3, respectively.

TABLE 2

| Gly + PBS solution | t/2 (sec) |
|---|---|
| Control | 11.87 |
| MeG | 346.6 |
| PrG | 239.0 |
| BuG | 385.1 |

TABLE 3

| DMSO | t/2 (sec) |
|---|---|
| Ctrl | 9.776 |
| MeG | 239.0 |
| PrG | 231.0 |
| BuG | 533.2 |
| OcG | 239.0 |

It was found that the half-life of the fluorescence intensity of PpIX in each solution is increased by about 20 folds in the presence of any alkyl gallate.

From the above, the present inventors surprisingly found that gallic acids have a superior inhibitory effect towards photobleaching of PpIX. In contrast, similar effect was not seen with PPD or DABCO, as well as ascorbic acid or α-tocopherol and the like known as reductants. Moreover, since photobleaching inhibitory effect for PpIX by gallic acids was also observed in cell lines having ALAs incorporated, it was shown that gallic acids will also be a superior photobleaching inhibitor in photodynamic diagnosis employing ALAs.

The invention claimed is:

1. A method for detecting a porphyrin accumulation site, comprising:
   irradiating a subject with the excitation light for porphyrins, wherein said subject has been administered in advance of said irradiation a precursor of porphyrins and a compound of the following formula (I):

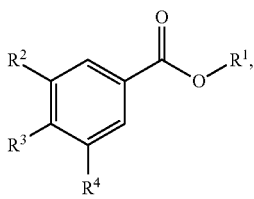

wherein $R^1$ is selected from the group consisting of an alkyl group having 1-10 carbons, a cycloalkyl group having 3-8 carbons, an aryl group having 6-14 carbons, and an aralkyl group having 7-15 carbons, and $R^2$, $R^3$, and $R^4$ each represent a hydroxyl group, or a salt thereof, said precursor of porphyrins and compound of formula (I) having been administered to said subject at simultaneous or different times, and detecting the fluorescence of porphyrins, thereby detecting the porphyrin accumulation site.

2. A photodynamic diagnostic method for measuring a range of a lesion site in a subject, comprising:

administering to said subject a precursor of porphyrins and a compound of the following formula (I):

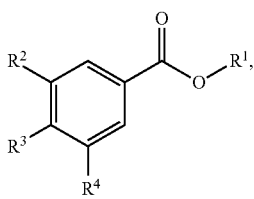

wherein $R^1$ is selected from the group consisting of an alkyl group having 1-10 carbons, a cycloalkyl group having 3-8 carbons, an aryl group having 6-14 carbons, and an aralkyl group having 7-15 carbons, and $R^2$, $R^3$, and $R^4$ each represent a hydroxyl group or a salt thereof, at simultaneous or different times, irradiating the subject with the excitation light for porphyrins, identifying the porphyrins accumulation site by detecting the fluorescence of porphyrins, and measuring the range of the lesion site.

3. The method according to claim 1, wherein $R^1$ is selected from the group consisting of a methyl group, a propyl group, a butyl group, and an octyl group.

4. The method according to claim 2, wherein $R^1$ is selected from the group consisting of a methyl group, a propyl group, a butyl group, and an octyl group.

5. The method according to claim 1, wherein said precursor of porphyrins is a 5-aminolevulinic acid (ALA).

6. The method according to claim 2, wherein said precursor of porphyrins is a 5-aminolevulinic acid (ALA).

7. The method according to claim 1, wherein said precursor of porphyrins is a compound of the following formula (II):

$$R^1\!-\!NHCH_2COCH_2CH_2COOR^2 \qquad (II),$$

wherein $R^1$ represents a hydrogen atom or an acyl group, and $R^2$ represents a hydrogen atom, a linear or branched alkyl group, a cycloalkyl group, an aryl group, or an aralkyl group, or a salt thereof.

8. The method according to claim 2, wherein said precursor of porphyrins is a compound of the following formula (II):

$$R^1\!-\!NHCH_2COCH_2CH_2COOR^2 \qquad (II),$$

wherein $R^1$ represents a hydrogen atom or an acyl group, and $R^2$ represents a hydrogen atom, a linear or branched alkyl group, a cycloalkyl group, an aryl group, or an aralkyl group, or a salt thereof.

9. The method according to claim 1, wherein said porphyrins are selected from the group consisting of protoporphyrin IX, uroporphyrin I, uroporphyrin III, coproporphyrin I, coproporphyrin III, heptacarboxylporphyrin I, heptacarboxylporphyrin III, hexacarboxylporphyrin I, hexacarboxylporphyrin III, pentacarboxylporphyrin I, pentacarboxylporphyrin III, isocoproporphyrin, harderoporphyrin, isoharderoporphyrin, mesoporphyrin IX, deuteroporphyrin IX, and pemptoporphyrin.

10. The method according to claim 2, wherein said porphyrins are selected from the group consisting of protoporphyrin IX, uroporphyrin I, uroporphyrin III, coproporphyrin I, coproporphyrin III, heptacarboxylporphyrin I, heptacarboxylporphyrin III, hexacarboxylporphyrin I, hexacarboxylporphyrin III, pentacarboxylporphyrin I, pentacarboxylporphyrin III, isocoproporphyrin, harderoporphyrin, isoharderoporphyrin, mesoporphyrin IX, deuteroporphyrin IX, and pemptoporphyrin.

11. The method according to claim 9, wherein said porphyrins are protoporphyrin IX (PpIX).

12. The method according to claim 10, wherein said porphyrins are protoporphyrin IX (PpIX).

* * * * *